United States Patent
Filić et al.

(10) Patent No.: US 6,767,917 B1
(45) Date of Patent: Jul. 27, 2004

(54) AMORPHOUS TORASEMIDE MODIFICATION

(75) Inventors: Darko Filić, Zagreb (HR); Miljenko Dumić, Zagreb (HR); Božena Klepić, Jastrebarsko (HR); Aleksandar Danilovski, Rijeka (HR); Marijan Tudja, Zagreb (HR)

(73) Assignee: Pliva d.d., Zagreb (HR)

( * ) Notice: Subject to any disclaimer, the term of this patent is extended or adjusted under 35 U.S.C. 154(b) by 0 days.

(21) Appl. No.: 10/239,024

(22) PCT Filed: May 2, 2000

(86) PCT No.: PCT/HR00/00011

§ 371 (c)(1),
(2), (4) Date: Mar. 17, 2003

(87) PCT Pub. No.: WO01/70694

PCT Pub. Date: Sep. 27, 2001

(30) Foreign Application Priority Data

Mar. 20, 2000 (HR) ........................ P20000162A

(51) Int. Cl.⁷ ...................... C07D 213/02; A61K 31/44
(52) U.S. Cl. ...................... 514/352; 546/291
(58) Field of Search ........................ 546/291; 514/352

(56) References Cited

U.S. PATENT DOCUMENTS 4,743,693 A * 5/1988 Topfmeier et al. .......... 546/291
5,700,820 A   12/1997 Vyas et al.
5,914,336 A * 6/1999 Dreckmann-Behrendt .. 514/347
6,465,496 B1  10/2002 Aronhime et al.

FOREIGN PATENT DOCUMENTS

| DE | 2516025 | 11/1975 |
| WO | WO 9000553 | 1/1990 |
| WO | WO 9626197 | 8/1996 |
| WO | WO 0020395 | 4/2000 |

OTHER PUBLICATIONS

L. Dupont et al., "Structure Cristalline et Moleculaire d' un Diuretique I'Alkyl–1'(Phenylamino–4–pyridyl–3)sulfonyl–3 Uree: la Torasemide (C15H20N4S03)" Acta Crystallogrphica, vol. B, No. 34, 1978, pp. 1304–1310.

L. Dupont et al., "Structure d' une Seconde Variete de la Torasumide", Acta Crystallographica, vol. B. No. 34, 1978, pp. 2659–2662.

B. Masereel et al., "Synthesis and Pharmacology of pyrid–3–ylsulfonylcyanoguanidines as diuretics", European Journal of Medicinal Chemistry, vol. 30, 1995, pp. 343–351.

* cited by examiner

*Primary Examiner*—Zinna Northington Davis
(74) *Attorney, Agent, or Firm*—Connoly Bove Lodge & Hutz LLP

(57) ABSTRACT

The present invention relates to an amorphous torasemide modification, to a process for preparation thereof, to its use as a raw material for the preparation of pharmaceutically acceptable salts of torasemide, to pharmaceutical forms containing the amorphous torasemide modification as well as to its use as a diuretic.

11 Claims, 3 Drawing Sheets

Fig. 1: DSC of the amorphous torasemide modification
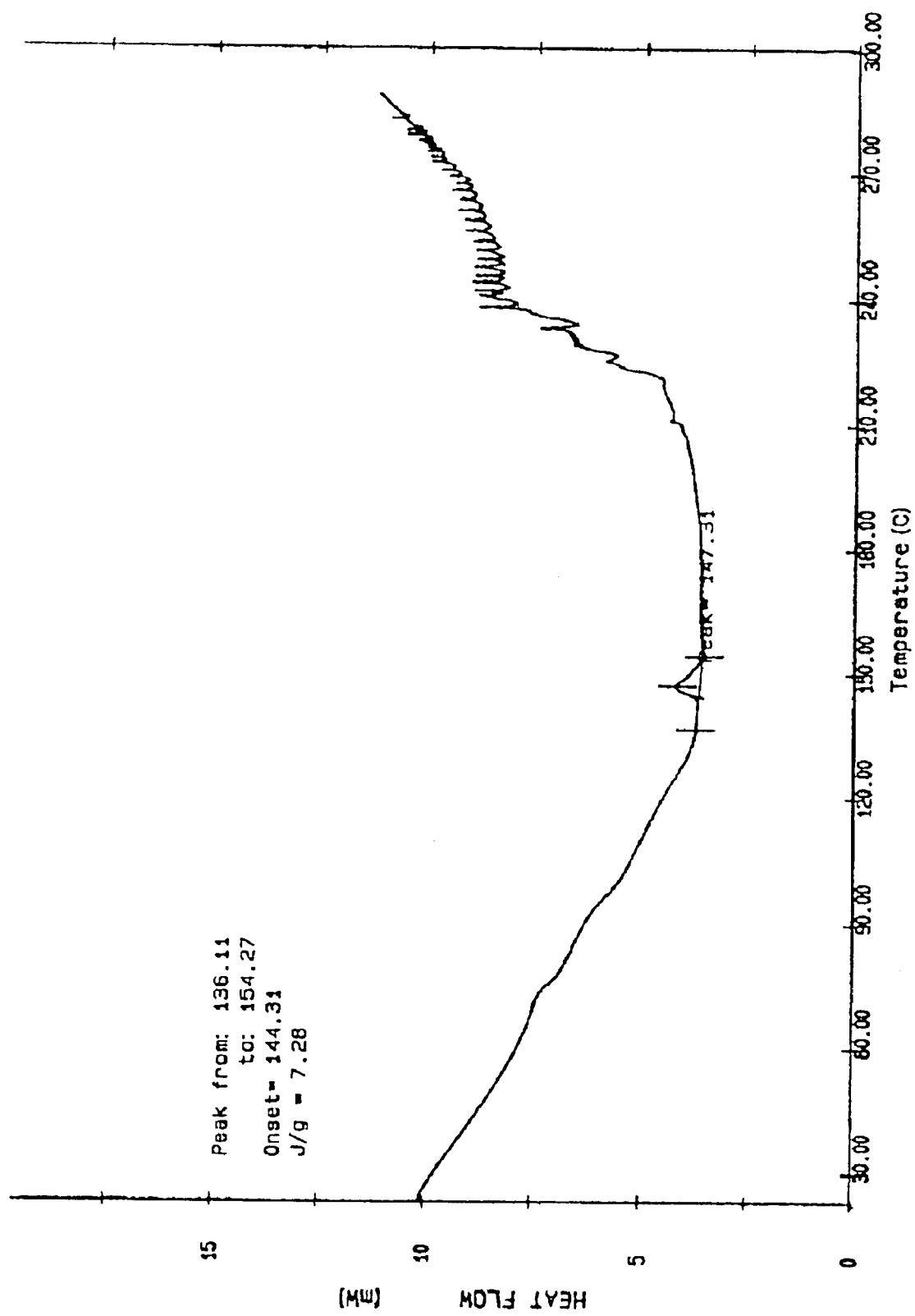

Fig. 2: X-ray powder pattern of a sample of the amorphous torasemide modification
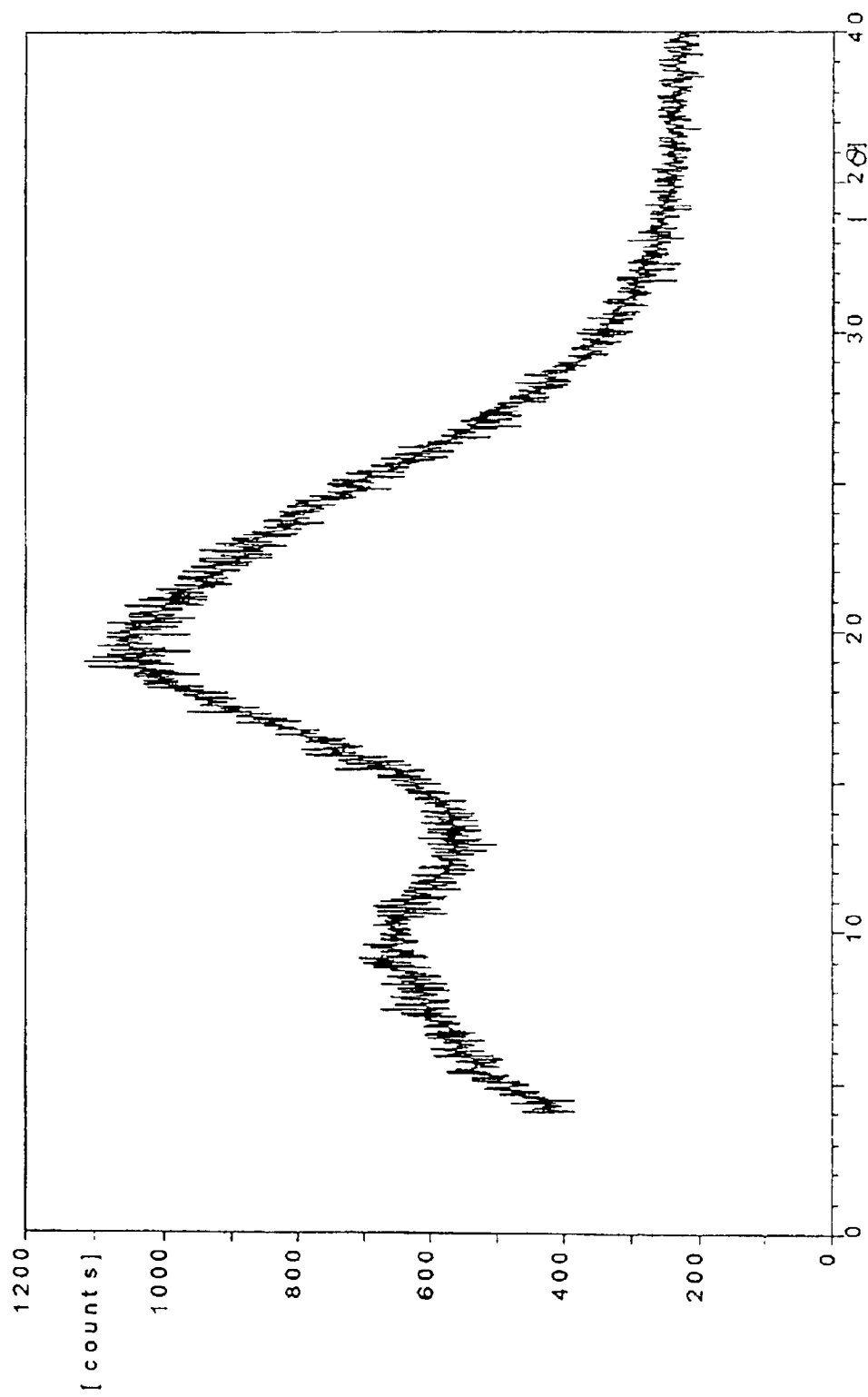

Fig. 3: IR spectrum of the amorphous torasemide modification recorded in KBr
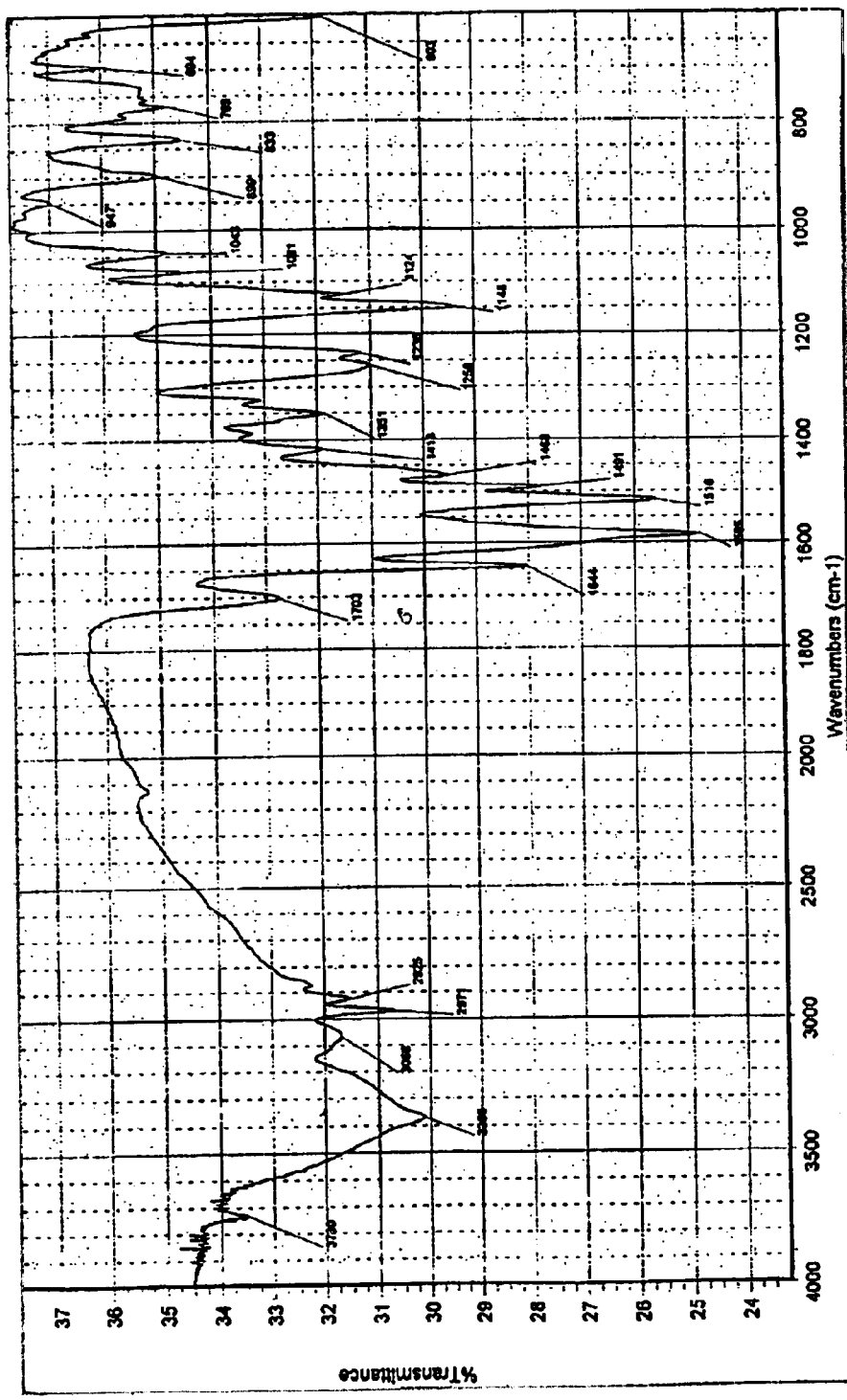

AMORPHOUS TORASEMIDE MODIFICATION

The present invention relates to an amorphous modification of N-(1-methylethyl aminocarbonyl)-4-(3-methylphenylamino)-3-pyridinesulfonamide (in the further text of the application designated by its generic name "torasemide"), to a process for its preparation, to its use as a raw material for pharmaceutically acceptable salts of torasemide, to pharmaceutical forms containing the said amorphous torasemide modification as the active ingredient as well as to its use as diuretic.

Torasemide is a new potential diuretic in the class of the so-called "loop diuretics", which is described in DE patent 25 16 025 (Example 71). Structurally, it entirely differs from diuretics of the same class such as furosemide, bumetanide and azosemide. In addition to diuretic properties it also possesses antihypertension properties.

As a diuretic of Henle's loop it is useful as an agent for preventing heart or heart tissue damages caused by metabolic or ionic abnormalities associated with ischemia, in the treatment of thrombosis, angina pectoris, asthma, hypertension, nephroedema, pulmonary edema, primary and secondary aldosteronism, Bartter's syndrome, tumours, glaucoma, decreasing of intraocular pressure, acute or chronic bronchitis, in the treatment of cerebral edema caused by trauma, ischemia, concussion of the brain, metastases or epileptic attacks and in the treatment of nasal infections caused by allergens.

The ability of a substance to exist in more than one crystal form is defined as polymorphism and these different crystal forms are named "polymorph modifications" or "polymorphs". In general, polymorphism is caused by the ability of the molecule of a substance to change its conformation or to form different intermolecular or intra-molecular interactions, particularly hydrogen bonds, which is reflected in different atom arrangements in the crystal lattices of different polymorphs. Polymorphism is found in several organic compounds. Among medicaments polymorphism is found in about 70% of barbiturates, 60% of sulfonamides and 60% of steroids, and about 50% of medicaments of the said classes are not present on the market in their most stable forms (T. Laird, Chemical Development and Scale-up in the Fine Chemical Industry, Principles and Practices, Course Manual, Scientific Update, Wyvern Cottage, 1996).

The different polymorphs of a substance possess different energies of the crystal lattice and, thus, they show different physical properties of the solid state such as form, density, melting point, colour, stability, dissolution rate, milling facility, granulation, compacting etc., which in medicaments may affect the possibility of the preparation of pharmaceutical forms, their stability, dissolution and bioavailability and, consequently, their action.

Polymorphism of medicaments is the object of studies of interdisciplinar expert teams [J. Haleblian, W. McCrone, *J. Pharm. Sci.* 58 (1969) 911; L. Borka, *Pharm. Acta Helv.* 66 (1991) 16; M. Kuhnert-Brandstätter, *Pharmazie* 51 (1996) 443; H. G. Brittain, *J. Pharm. Sci.* 86 (1997) 405; W. H. Streng, *DDT* 2 (1997) 415; K. Yoshii, *Chem. Pharm. Bull.* 45 (1997) 338, etc.]. A good knowledge of polymorphism represents a precondition for a critical observation of the whole process of medicament development. Thus, at deciding on the production of a pharmaceutical form in solid state and with regard to the dose size, stability, dissolution and anticipated action, it is necessary to determine the existence of all solid state forms (on the market some computer programmes can be found, e.g. >>Polymorph<< as a module of >>Cerius2<< programme, MSI Inc., USA) and to determine the physical-chemical properties of each of them. Only on the basis of these determinations the appropriate polymorph can be selected for the development of pharmaceutical formulations of desired properties.

From the great number of such efforts only a few will be mentioned as an example. Thus, Chikaraishi et al. (WO 9626197) protected, in addition to a polimorph form, also an amorphous form of piretanide as well as processes for preparation thereof. J.-B. Cha et al. (WO 9857967) protected an amorphous form, a process for the preparation thereof and pharmaceutical formulations of the medicament itraconazole containing this amorphous form; E. Occeli et al. (WO 9000553) protected crystal polimorphs I and II and the amorphs of the medicament rifapentine hydrochloride and hydrobromide. Further, for the new antidiabetic troglitazone G. Om Reddy et al. (U.S. Pat. No. 5,700,820) protected six polimorphs: five crystal polimorphs and one amorphous one.

It is known that torasemide can exist in three crystal modifications differing with regard to the parameters of a single cell, which is confirmed by X-ray diffraction on their monocrystals. Modification I with melting point 169° C. [*Acta Cryst* . . . B34 (1978), 1304–1310] and modification III with melting point 165° C. [HR patent application P980532A (U.S. patent application Ser. No. 09/187046)] crystallize monoclinically in the space group P $2_1$/c (prisms), while modification II with melting point 162° C. crystallizes monoclinically in the space group P 2/n (foils) [*Acta Cryst*. B34 (1978), 2659–2662].

In addition to the above, U.S. Pat. No. 5,914,336 protected the use of a new torasemide polimorph, however, only some of its physical-chemical properties such as melting point, heat of formation, solubility, first band in IR-spectrum, but no X-ray patterns of the powder and monocrystal were stated.

In our further research in the field of torasemide we have surprisingly found an amorphous torasemide modification which has hitherto not been known.

The amorphous torasemide modification has the form of an amorphous voluminous powder, which—in the same way as the powder obtained by the grinding thereof—does not show any diffraction maxima at recording the X-ray powder pattern, which demonstrates the amorphous nature thereof.

In the solution the amorphous modification is identical with other known torasemide modifications, which is evident from NMR and UV spectra. On the other hand, solid state analysis techniques such as differential scanning calorimetry (DSC), X-ray powder pattern (XRD) and IR spectroscopy reveal the difference in comparison to the known torasemide modifications.

DSC of the amorphous torasemide modification (FIG. 1) shows one exothermic maximum at about 147° C. (onset at about 144° C.) resulting from decomposition (also evident on the basis of IR spectroscopy and thin-layer chromatography).

The X-ray powder pattern of the amorphous torasemide modification differs from the X-ray powder patterns of the known torasemide modifications and does not show any diffraction maxima, which confirms the amorphous nature (FIG. 2).

The IR spectrum of a sample of the amorphous modification recorded in KBr (FIG. 3) differs from IR spectra of the known torasemide modifications. The amorphous torasemide modification shows characteristic absorption bands at 2900 to 3366 cm$^{-1}$ and at 1400 to 1703 cm$^{-1}$.

BRIEF DESCRIPTION OF THE DRAWING

FIG. 1 represents a characteristic thermogram of differential scanning calorimetry (DSC) of the amorphous torasemide modification.

FIG. 2 represents a characteristic X-ray powder pattern of the amorphous torasemide modification.

FIG. 3 represents a characteristic IR spectrum of the amorphous torasemide modification recorded in KBr.

The amorphous torasemide modification according to the present invention can be obtained by dissolving modifications I, II or III or an amorphous torasemide modification or any mixture thereof in water with or without the addition of a base and a subsequent removal of the water and base from such solutions.

The process for the preparation of an amorphous torasemide modification comprises:
 (i) the preparation of torasemide polimorph I according to a known process,
 (ii) the dissolution of polimorph I in water with or without the addition of a base at a temperature from 5 to 100° C. within 5 minutes to 24 hours,
 (iii) the filtration of the obtained solution,
 (iv) the cooling of the obtained solution at a temperature from −20° C. to −70° C.,
 (v) the removal of water and the base from the frozen solution in order to prepare an amorphous torasemide modification, which is characterized by the following data:
  DSC: exothermic maximum at about 147° C. (onset at about 144° C.) (FIG. 1);
  X-ray powder pattern (2 Θ): no diffraction maxima due to the amorphous nature (FIG. 2);
  IR-characteristic absorption bands ($cm^{-1}$): at 2900 to 3366 and at 1400 to 1703 (FIG. 3).

According to a further embodiment of the present invention the process for the preparation of an amorphous torasemide modification also comprises:
 (i) the preparation of torasemide polimorph II according to a known process,
 (ii) the dissolution of polimorph II in water with or without addition of a base at a temperature from 5 to 100° C. within 5 minutes to 24 hours,
 (iii) the filtration of the obtained solution,
 (iv) the cooling of the obtained solution at a temperature from −20° C. to −70° C.,
 (v) the removal of water and the base from the frozen solution in order to prepare an amorphous torasemide modification, which is characterized by the data represented in the previous process.

According to a further embodiment of the present invention the process for the preparation of an amorphous torasemide modification also comprises:
 (i) the preparation of torasemide polimorph III according to a known process,
 (ii) the dissolution of polimorph III in water with or without the addition of a base at a temperature from 5 to 100° C. within 5 minutes to 24 hours,
 (iii) the filtration of the obtained solution,
 (iv) the cooling of the obtained solution at a temperature from −20° C. to −70° C.,
 (v) the removal of water and the base from the frozen solution in order to prepare an amorphous torasemide modification, which is characterized by the data represented in the previous process.

According to a further embodiment of the present invention the process for the preparation of an amorphous torasemide modification also comprises:
 (i) the preparation of an amorphous torasemide modification according to the process of the present invention,
 (ii) the dissolution of the amorphous torasemide modification in water with or without the addition of a base at a temperature from 5 to 100° C. within 5 minutes to 24 hours,
 (iii) the filtration of the obtained solution,
 (iv) the cooling of the obtained solution at a temperature from −20° C. to −70° C.,
 (v) the removal of water and the base from the frozen solution in order to prepare an amorphous torasemide modification, which is characterized by the data represented in the previous process.

According to a further embodiment of the present invention the process for the preparation of an amorphous torasemide modification also comprises:
 (i) the preparation of torasemide polimorphs I, II and III according to known processes and the preparation of an amorphous torasemide modification according to the process of the present invention,
 (ii) the dissolution of any mixture of the torasemide polimorphs I, II and III or of the amorphous torasemide modification in water with or without the addition of a base at a temperature from 5 to 100° C. within 5 minutes to 24 hours,
 (iii) the filtration of the obtained solution,
 (iv) the cooling of the obtained solution at a temperature from −20° C. to −70° C.,
 (v) the removal of water and the base from the frozen solution in order to prepare an amorphous torasemide modification, which is characterized by the data represented in the previous process .

According to the process of the present invention, an aqueous ammonia solution is used as the base for the preparation of the aforementioned aqueous torasemide solutions.

According to the process of the present invention, lyophilization is used as the method for the removal of the water and the base.

It has been found that by the use of the process of the invention no decomposition of torasemide takes place, i.e. a chemically pure amorphous torasemide modification is obtained (TLC and HPLC).

It has also been found that the amorphous torasemide modification is stable under normal storage conditions, at crushing and compressing, i.e. it does not convert into a crystal modification I, II or III of torasemide.

The amorphous torasemide modification prepared according to the present process can be converted to crystal modifications I, II and II of torasemide by conventional processes, i.e. it may be used as a starting material for the preparation of the known crystal modifications I, II and III of torasemide.

The amorphous torasemide modification prepared according to the present invention can be converted into pharmaceutically acceptable salts of torasemide by means of conventional processes.

The research of the release (USP 24) of the amorphous torasemide modification in water in comparison with the profile of the release of the known crystal torasemide modifications in the same medium has shown its slower release. The amorphous torasemide modification as such is suitable for the preparation of pharmaceutical prepartions having short-term or prolonged actions.

The amorphous torasemide modification prepared according to the process of the present invention is a suitable torasemide form to be used as a diuretic and as an agent for preventing heart or heart tissue damages caused by metabolic or ionic abnormalities associated with ischemia, in the treatment of thrombosis, angina pectoris, asthma, hypertension, nephroedema, pulmonary edema, primary and secondary aldosteronism, Bartter's syndrome, tumours, glaucoma, for decreasing intraocular pressure, acute or chronic bronchitis, in the treatment of cerebral edema caused by trauma, ischemia, concussion of the brain, metastases or epileptic attacks and in the treatment of nasal infections caused by allergens.

The present invention also relates to pharmaceutical forms such as tablets, capsules and injection containing an effective amount of the amorphous torasemide modification as the active ingredient without any additives or combined with one or more pharmaceutically acceptable additives such as sugar, starch, starch derivatives, cellulose, cellulose derivatives, mould release agents, and antiadhesive agents and possibly agents for flowability regulation.

This present invention is illustrated but in no way limited by the following Examples.

EXAMPLE 1

The crystal modification I of torasemide (3.00 g) prepared according to *Acta Cryst.* B34 (1978) 1304–1310 was suspended in 60 ml of demineralised water at 25° C., 30 drops of an aqueous ammonia solution were added and the obtained solution was stirred at the same temperature for 24 hours and then filtered. Subsequently, the solution was frozen at a temperature of about –70° C., whereupon the water and ammonia were removed by lyophilization.

After isolation from the lyophilization vessel there were obtained 2.87 g of an amorphous torasemide modification; melting point (apparatus for melting point determination: Büchi 535): start of softening at about 80° C., decomposition at about 148° C.

The characteristic IR spectrum of the sample as shown in FIG. 3 was recorded in KBr in the IR-spectrophotometer Nicolet-Magna 760.

The characteristic X-ray powder pattern as shown in FIG. 2 was recorded in the instrument PHILIPS PW3710 under Cu X-rays [$\lambda(CuK\alpha_1)=1.54046$ and $\lambda(CuK\alpha_2)=1.54439$].

The characteristic DSC curve of the sample as shown in FIG. 1 was recorded in the apparatus Perkin-Elmer DSC7 at a heating rate of 5° C./minute.

EXAMPLE 2

The crystal modification I of torasemide (0.08 g) prepared according to *Acta Cryst.* B34 (1978) 1304–1310 was dissolved under stirring in 50 ml of demineralised water at a temperature of about 80° C. within 3 hours, whereupon the solution was cooled to room temperature and filtered. Subsequently, the solution was frozen at a temperature of about –50° C. and the water was removed by lyophilization.

After isolation from the lyophilization vessel there were obtained 0.05 g of an amorphous torasemide modification; melting point (apparatus for melting point determination: Büchi 535): start of softening at about 80° C., decomposition at about 148° C.

The IR spectrum of the thus obtained sample corresponded to the IR spectrum of the new amorphous modification obtained in Example 1.

EXAMPLE 3

The crystal modification II of torasemide (1.00 g) prepared according to *Acta Cryst.* B34 (1978) 1304–1310 was suspended in 50 ml of demineralised water at 10° C., 10 drops of an aqueous ammonia solution were added and the obtained solution was stirred at the same temperature for 12 hours and then filtered. Subsequently, the solution was frozen at a temperature of about –60° C., whereupon the water and ammonia were removed by lyophilization.

After isolation from the lyophilization vessel there were obtained 0.98 g of an amorphous torasemide modification; melting point (apparatus for melting point determination: Büchi 535): start of softening at about 80° C., decomposition at about 148° C.

The IR spectrum of the thus obtained sample corresponded to the IR spectrum of the new amorphous modification obtained in Example 1.

EXAMPLE 4

The crystal modification III of torasemide (1.00 g) prepared according to HR patent application P980532A (U.S. patent application Ser. No. 09/187046) was suspended in 50 ml of demineralised water at 20° C., 10 drops of an aqueous ammonia solution were added and the obtained solution was stirred at the same temperature for 5 hours and then filtered. Subsequently, the solution was frozen at a temperature of about –60° C., whereupon the water and ammonia were removed by lyophilization.

After isolation from the lyophilization vessel there were obtained 0.98 g of an amorphous torasemide modification; melting point (apparatus for melting point determination: Büchi 535): start of softening at about 80° C., decomposition at about 148° C.

The IR spectrum of the thus obtained sample corresponded to the IR spectrum of the new amorphous modification obtained in Example 1.

EXAMPLE 5

A mixture (0.08 g) of crystal modifications I and II of torasemide prepared according to *Acta Cryst.* B34 (1978) 1304–1310 was dissolved under stirring in 60 ml of demineralised water at a temperature of about 90° C. within 10 hours, whereupon the solution was cooled to room temperature and filtered. Subsequently, the solution was frozen at a temperature of about –40° C. and then the water was removed by lyophilization.

After isolation from the lyophilization vessel there were obtained 0.06 g of an amorphous torasemide modification; melting point (apparatus for melting point determination: Büchi 535): start of softening at about 80° C., decomposition at about 148° C.

The IR spectrum of the thus obtained sample corresponded to the IR spectrum of the new amorphous modification obtained in Example 1.

EXAMPLE 6

A mixture (0.08 g) of crystal modifications II and III of torasemide prepared according to *Acta Cryst.* B34 (1978) 1304–1310 and HR patent application P980532A (U.S. patent application Ser. No. 09/187046) was dissolved under stirring in 60 ml of demineralised water at a temperature of about 100° C. within 5 hours, whereupon the solution was cooled to room temperature and filtered. Subsequently, the solution was frozen at a temperature of about –50° C. and then the water was removed by lyophilization.

After isolation from the lyophilization vessel there were obtained 0.07 g of an amorphous torasemide modification; melting point (apparatus for melting point determination: B üchi 535): start of softening at about 80° C., decomposition at about 148° C.

The IR spectrum of the thus obtained sample corresponded to the IR spectrum of the new amorphous modification obtained in Example 1.

EXAMPLE 7

A mixture (1.00 g) of crystal modifications I and III of torasemide prepared according to *Acta Cryst.* B34 (1978) 1304–1310 and HR patent application P980532A (U.S. patent application Ser. No. 09/187046) was suspended in 50 ml of demineralised water at 5° C., 10 drops of an aqueous ammonia solution were added and then the solution was stirred at the same temperature for 18 hours, whereupon it was filtered. Subsequently, the solution was frozen at a temperature of about −60° C. and then the water and ammonia were removed by the lyophilization.

After isolation from the lyophilization vessel there were obtained 0.98 g of an amorphous torasemide modification; melting point (apparatus for melting point determination: B üchi 535): start of softening at about 80° C., decomposition at about 1480C.

The IR spectrum of the thus obtained sample corresponded to the IR spectrum of the new amorphous modification obtained in Example 1.

EXAMPLE 8

The amorphous torasemide modification (3.0 g) prepared according to Example 1 of the present invention was suspended in 60 ml of demineralised water at 25° C., 30 drops of an aqueous ammonia solution were added and the obtained solution was stirred at the same temperature for 30 minutes and then filtered. Subsequently, the solution was frozen at a temperature of about −30° C., whereupon the water and ammonia were removed by lyophilization.

After isolation from the lyophilization vessel there were obtained 2.94 g of an amorphous torasemide modification; melting point (apparatus for melting point determination: B üchi 535): start of softening at about 800° C., decomposition at about 148° C.

The IR spectrum of the thus obtained sample corresponded to the IR spectrum of the new amorphous modification obtained in Example 1.

EXAMPLE 9

A mixture (1.20 g) of crystal modifications I, II and III of torasemide prepared according to *Acta Cryst.* B34 (1978) 1304–1310 and HR patent application P980532A (U.S. patent application Ser. No. 09/187046) and of the amorphous torasemide modification prepared according to Example 1 of the present invention was suspended in 60 ml of demineralised water at 25 ° C., 10 drops of an aqueous ammonia solution were added and the obtained solution was stirred at the same temperature for 30 minutes, whereupon it was filtered. Subsequently, the solution was frozen at a temperature of about −30° C. and then the water and ammonia were removed by the lyophilization.

After isolation from the lyophilization vessel there were obtained 1.18 g of an amorphous torasemide modification; melting point (apparatus for melting point determination: B üchi 535): start of softening at about 80° C., decomposition at about 148° C.

The IR spectrum of the thus obtained sample corresponded to the IR spectrum of the new amorphous modification obtained in Example 1.

EXAMPLE 10

The amorphous torasemide modification prepared according to Example 1 of the present invention was subjected to the test of the release of the active substance in water at a temperature of 37° C. (USP 24) and the results are represented in Table 1.

TABLE 1

Release of the amorphous torasemide modification in water (USP 24) (37° C., 50 rpm, 1000 ml)

| Time (minutes) | Released torasemide (%) |
|---|---|
| 0 | 0 |
| 15 | 6.8 |
| 30 | 10.2 |
| 45 | 13.0 |
| 60 | 15.9 |
| 90 | 20.4 |
| 120 | 24.9 |

What is claimed is:

1. Amorphous torasemide modification having the following data: DSC: exothermic maximum at about 147° C. (onset at about 144° C.); X-ray powder pattern (2 Θ): no diffraction maxima due to the amorphous nature; IR characteristic absorption bands at 2900 to 3366 cm$^{-1}$ and at 1400 to 1703 cm$^{-1}$.

2. Amorphous torasemide modification according to claim 1, being chemically pure.

3. Process for the preparation of the amorphous torasemide modification according to claim 1, which comprising dissolving torasemide modifications in water with or without the addition of a base at a temperature from 5° C. to 100° C. within 5 minutes to 24 hours and then cooling the solutions to a temperature from −20° C. to −70° C. and removing water.

4. Process for the preparation of the amorphous torasemide modification according to claim 3, wherein the torasemide modifications are selected from the group consisting of crystal torasemide modifications I, II or III, an amorphous torasemide modification thereof, any mixture of the crystal torasemide modifications I, II and II and an amorphous torasemide modification.

5. Process for the preparation of the amorphous torasemide modification according to claim 3 wherein a base is used and the base comprises aqueous ammonia solution.

6. Process for the preparation of the amorphous torasemide modification according to claim 3 wherein removing the water and the base, if present, comprises lyophilization.

7. A pharmaceutically acceptable salt of the amorphous torasemide modification according to claim 1.

8. A method for treating a patient in need of at least one of a diuretic, an agent for preventing heart or heart tissue damages caused by metabolic or ionic abnormalities associated with ischemia, a treatment for thrombosis, angina pectoris, asthma, hypertension, nephroedema, pulmonary edema, primary and secondary aldosteronism, Barrier's syndrome, tumour, glaucoma, for decreasing intraocular pressure, acute or chronic bronchitis, a treatment for cerebral edema caused by trauma, ischemia, concussion of the brain, metastases or epileptic attacks and a treatment for nasal infections caused by allergens which comprises administering to said patient an effective amount of the amorphous torasemide modification according to claim 1.

9. A pharmaceutical composition comprising as an active ingredient, an effective amount of the amorphous torasemide modification according to claim 1 and optically one or more pharmaceutically acceptable additives.

10. A pharmaceutical composition according to claim 9, being in the form of a tablet, a capsule or an injectable.

11. The pharmaceutical composition according to claim 9 wherein the additive comprise at least one member selected from the group consisting of sugar, starch, starch derivatives, cellulose, cellulose derivatives, mould release agents, antiadhesive agents, and flowability regulation agents.

* * * * *